(12) United States Patent
Baucke et al.

(10) Patent No.: US 6,440,937 B1
(45) Date of Patent: Aug. 27, 2002

(54) DIPEPTIDE BENZAMIDINE AS A KININOGENASE INHIBITOR

(75) Inventors: Dorit Baucke, Mannheim; Udo Lange; Helmut Mack, both of Ludwigshafen; Thomas Pfeiffer, Böhl-Iggelheim; Werner Seitz, Plankstadt; Thomas Zierke, Böhl-Iggelheim; Hans Wolfgang Höffken, Ludwigshafen; Wilfried Hornberger, Neustadt, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/242,126

(22) PCT Filed: Jul. 29, 1997

(86) PCT No.: PCT/EP97/04105

§ 371 (c)(1),
(2), (4) Date: Feb. 10, 1999

(87) PCT Pub. No.: WO98/06740

PCT Pub. Date: Feb. 19, 1998

(30) Foreign Application Priority Data

Aug. 14, 1996 (DE) ........................... 196 32 772

(51) Int. Cl.⁷ .................................. C07K 5/06
(52) U.S. Cl. .................. 514/19; 514/20; 530/331; 548/535
(58) Field of Search .............. 514/19, 20; 530/331; 548/535

(56) References Cited

FOREIGN PATENT DOCUMENTS

| EP | 601459 | 6/1994 |
|----|--------|--------|
| WO | 94/29336 | 12/1994 |
| WO | 95/23609 | 9/1995 |
| WO | 95/35309 | 12/1995 |
| WO | 96/25426 | 8/1996 |
| WO | 98/06741 | 2/1998 |

*Primary Examiner*—Christopher S. F. Low
*Assistant Examiner*—David Lukton
(74) *Attorney, Agent, or Firm*—Keil & Weinkauf

(57) ABSTRACT

Compounds of the formula I

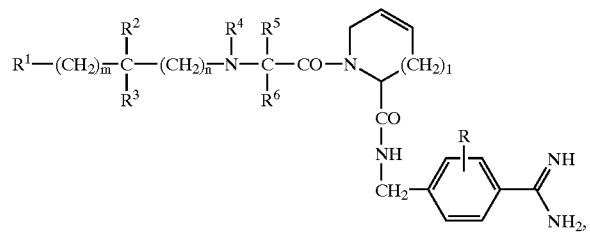

where R, $R^1$, $R^2$, $R^3$, $R^4$, $R^5$ and $R^6$, and l, m and n have the meanings stated in the description, and their preparation are described. The novel compounds are suitable for controlling diseases.

16 Claims, No Drawings

DIPEPTIDE BENZAMIDINE AS A KININOGENASE INHIBITOR

TECHNICAL FIELD

Thrombin belongs to the group of serine proteases and plays a central part in the blood coagulation cascade as terminal enzyme. Both the intrinsic and the extrinsic coagulation cascades lead via a plurality of amplifying stages to the production of thrombin from prothrombin. Thrombin-catalyzed cleavage of fibrinogen to fibrin then initiates blood coagulation and aggregation of platelets which, in turn, due to the binding of platelet factor 3 and coagulation factor XIII, and a large number of highly active mediators, enhance thrombin formation.

The formation and action of thrombin are central events in the development both of white, arterial and of red, venous thrombi and are therefore potentially effective points of attack for drugs. Thrombin inhibitors are, by contrast with heparin, able independently of cofactors completely to inhibit simultaneously the effects of free thrombin and of that bound to platelets. They are able to prevent in the acute phase thromboembolic events after percutaneous transluminal coronary angioplasty (PTCA) and lysis, and to act as anticoagulants in extracorporeal circulation (heart-lung machine, hemodialysis). They can also be used generally for the prophylaxis of thrombosis, for example after surgical operations.

BACKGROUND ART

It is known that synthetic arginine derivatives influence the enzymatic activity of thrombin by interacting with the active serine residue of the protease thrombin. Peptides based on Phe-Pro-Arg in which the N-terminal amino acid is in the D form have proven particularly beneficial. D-Phe-Pro-Arg isopropyl ester is described as a competitive thrombin inhibitor (C. Mattson et al., Folia Haematol, 109 (1983) 43–51).

Derivatization of the arginine at the C terminus to the aldehyde leads to an enhancement of the inhibitory effect. Thus, a large number of arginals able to bind the hydroxyl group of the "active" serine in a hemiacetal have been described (EP 185390, 479489, 526877, 542525; WO 93/15756, 93/18060).

The thrombin-inhibitory activity of peptide ketones, fluorinated alkyl ketones and of keto esters, boric acid derivatives, phosphoric esters and a-keto carboxamides can likewise be explained by this serine interaction (EP 118280, 195212, 362002, 364344, 410411, 471651, 589741, 293881, 503203, 504064, 530167; WO 92/07869, 94/08941).

The peptide 4-amidinophenylglycinephosphonate diphenyl esters described by J. Oleksyszyn et al. in J. Med. Chem. 37 (1994) 226–231 are irreversible thrombin inhibitors with inadequate selectivity in respect of other serine proteases.

DE 3 108 810, WO 93/11152 and EP 601 459 describe agmatine and hence arginine derivatives which are unable to interact with the active serine in serine proteases.

WO 94/29336, EP 0 601 459 and WO 95/23609 represent a further development in which the agmatine is replaced by an arylamidine residue.

Kininogenases are serine proteases which liberate vasoactive peptides, called kinins (bradykinin, kallidin and Met-Lys-bradykinin), from kininogens. Kininogens are multifunctional proteins which occur in coagulation and inflammation cascade reactions. As inhibitors, they protect cells from damage by cysteine proteases (Müller Esterl, FEBS Lett. 182 (1985) 310–314).

Important kininogenases are plasma kallikrein, tissue kallikrein and mast cell tryptase.

Kinins like bradykinin and kallidin are vasoactive peptides which influence a large number of biological processes. They play an essential part in inflammatory processes. By increasing vascular permeability, they lead to hypotension and edema. Furthermore, they are very potent pain-producing autacoids and have great importance as cellular mediators in the pathophysiology of asthma, of allergic rhinitis and of arthritis (K. D. Bhoola, C. D. Figueroa, K. Worthy, Pharmacological Reviews 44 (1992)1–80).

Irrespective of the mechanisms underlying inflammatory processes, fluid containing all the protein systems in the circulating blood escapes from blood vessels. This means that escape of plasma fluid from vessels is involved in diseases such as asthma, rhinitis and inflammatory internal diseases. Moreover, mast cell tryptase is released particularly in allergic processes (Salomonsson et al., Am. Rev. Respir. Dis., 1992, 146, 1535–1542).

The arginine chloromethyl ketones H-(D)-Pro-Phe-Arg-$CH_2Cl$ and H-(D)-Phe-Phe-Arg-$CH_2$-Cl have been described by Kettner and Shaw as plasma kallikrein inhibitors (Biochem. 17 (1978) 4778–4784 and Meth. Enzym. 80 (1981) 826–842).

Various synthetic derivatives of benzamidines and benzylamines have proven to be inhibitors of plasma kallikrein, with the benzamidines having a considerably stronger inhibitory effect (F. Markward, S. Drawert, P. Walsmann, Biochemical Pharmacology 23 (1974) 2247–2256).

PKSI-527, the hydrochloride of N-(trans-4-aminomethylcyclo-hexylcarbonyl)-L-phenylalanin-4-carboxymethylanilide, is also an effective inhibitor of this kininogenase (Wanaka, Ohamoto et al., Thromb. Res., 57 (1990) 889–895).

DISCLOSURE OF INVENTION

The present invention relates to novel benzamidines, to their preparation and to their use as competitive inhibitors of trypsin-like serin proteases, especially thrombin and kininogenases such as kallikrein. The invention also relates to pharmaceutical compositions which contain the compounds as active ingredients, and to the use of the compounds as thrombin inhibitors, anticoagulants and antiinflammatory agents.

The invention relates to compounds of the formula I

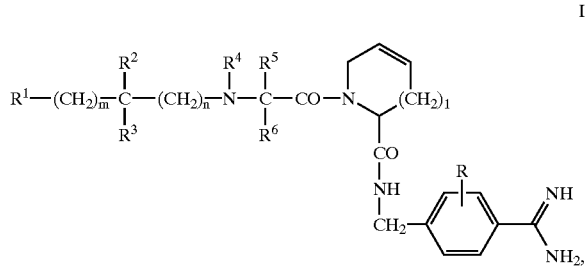

where R, $R^1$, $R^2$, $R^3$, $R^4$, $R^5$ and $R^6$, and l, m and n have the following meanings:

l 0 or 1, m 0, 1 or 2, n 0, 1 or 2,

R H or $C_{1-4}$-alkyl-, $R^1$ HOOC—, $C_{1-6}$-alkyl-OOC—, benzyl-OOC— or —OH, $R^2$ H—, $C_{1-4}$-alkyl- or $R^1$—$(CH_2)_m$—, $R^3$ H— or $C_{1-4}$-alkyl- which can be substituted by —OH or —COOH, $R^4$ H—, $C_{1-4}$-alkyl-, HOOC—$C_{1-4}$-alkylene-, $R^5$ $C_{1-8}$-alkyl-, cycloalkyl-$(CR^8R^9)_r$—, (r=0 or 1, $R^8$, $R^9$=H—, cycloalkyl- or $C_{1-4}$-alkyl-), in which up to four $CH_2$ groups in the cycloalkyl radical can be replaced, independently of one another, by $CR^{10}R^{11}$ ($R^{10}$=H— or $C_{1-4}$-alkyl-, $R^{11}$=$C_{1-4}$-alkyl-) and/or the CH group in the cycloalkyl radical which is bonded $CR^8R^9$ can be replaced by $CR^{12}$ ($R^{12}$=$C_{1-4}$-alkyl-), and/or one or two C—C single bond(s) in the ring can be replaced by a C=C double bond, $R^6$ H—, $C_{1-4}$-alkyl- or $R^4$ and $R^5$ together —$CH_2$—$CH_2$—$CH(R^7)$—, ($R^7$=H—, phenyl- or cyclohexyl-)

$R^2$ and $R^5$ together —$CH_2$—$CH_2$— or —$CH_2$—$CH_2$—$CH_2$—, in which one hydrogen atom can be replaced by $C_{1-4}$-alkyl-, phenyl- or cycloalkyl-, and salts thereof with physiologically tolerated acids.

The amino acid residues represented by —$NR^4$—C($R^5R^6$)—CO— preferably have the (D) configuration, and 3,4-dehydroproline and 4,5-dehydropipecolic acid preferably have the (L) configuration.

Preferred compounds of the formula I are those where

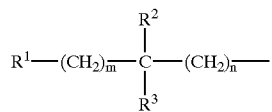

is HOOC—$(CH_2)_t$— (t=1, 2 or 3), (HOOC—$CH_2)_2$—CH—, (HO—$CH_2)_2$CH—, HOOC—$CH_2$—CH(COOH)—, HOOC—CH($CH_2$—$CH_2$—OH)—, HOOC—CH($C_{1-4}$-alkyl-), $C_{1-4}$-alkyl-OOC—$CH_2$—, benzyl-OOC—$CH_2$—, and where

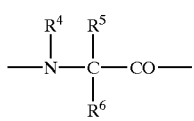

is

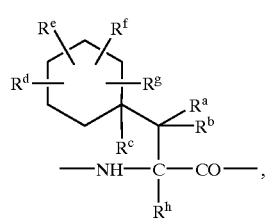

($R^a$, $R^b$=H, cyclohexyl- or $C_{1-4}$-alkyl-) ($R^c$, $R^d$, $R^e$, $R^f$, $R^g$, $R^h$=H— or $C_{1-4}$-alkyl-, where the $CH_2$-group of the ring can be mono- or disubstituted),

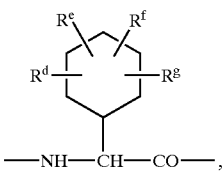

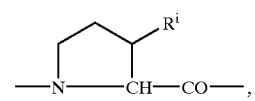

($R^i$=phenyl- or cyclohexyl-)

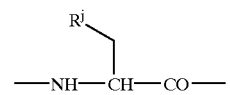

($R^j$=cyclopentyl-, cycloheptyl-, 1-adamantyl-, 1-norbornyl-, 1-bicyclo[2.2.2]octyl-, neopentyl-, tert-butyl-, diisopropylmethyl- or 1-(1,4-cyclohexadienyl-))

where this building block preferably has the D configuration, l is 0 and

R is H— or $CH_3$—.

Further preferred compounds of the formula I are those where

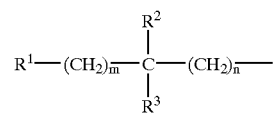

is HOOC—$(CH_2)_t$— (t=1, 2 or 3), (HOOC—$CH_2)_2$—CH—, (HO—$CH_2)_2$CH—, HOOC—$CH_2$—CH(COOH)—, HOOC—CH($CH_2$—$CH_2$—OH)—, HOOC—CH($C_{1-4}$-alkyl)-, $C_{1-4}$-alkyl-OOC—$CH_2$—, benzyl-OOC—$CH_2$, and where

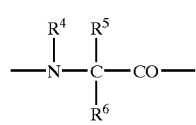

is

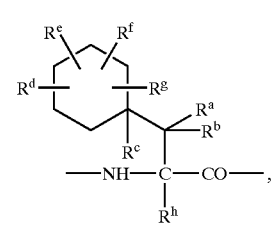

($R^a$, $R^b$=H, cyclohexyl- or $C_{1-4}$-alkyl-) ($R^c$, $R^d$, $R^e$, $R^f$, $R^g$, $R^h$=H— or $C_{1-4}$-alkyl-, where the $CH_2$ groups of the ring can be mono- or disubstituted),

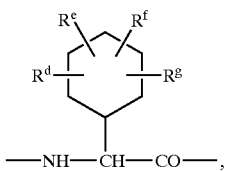

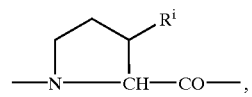

($R^i$=phenyl- or cyclohexyl-)

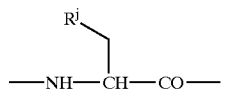

($R^j$=cyclopentyl-, cycloheptyl-, 1-adamantyl-, 1-norbornyl-, 1-bicyclo[2.2.2]octyl-, neopentyl-, tert-butyl-, diisopropylmethyl- or 1-(1,4-cyclohexadienyl-))
where this building block preferably has the D configuration,
l is 1 and
R is H— or $CH_3$—.

Also preferred are compounds having the structural element of the formula

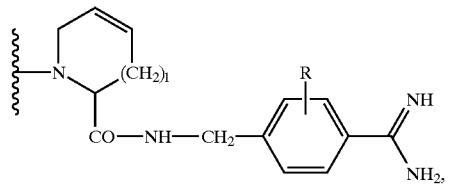

where l is 0 or 1 and R is H or $C_1$–$C_4$-alkyl, in particular $CH_3$. Preferred intermediates are compounds of the formula II

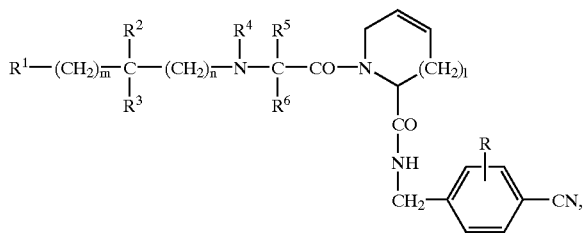

where

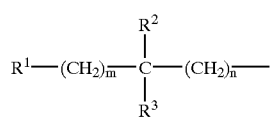

is HOOC—$(CH_2)_t$— (t=1, 2 or 3), (HOOC—$CH_2)_2$—CH—, (HO—$CH_2)_2$CH—, HOOC—$CH_2$—CH(COOH)—, HOOC—CH($CH_2$—$CH_2$—OH)—, HOOC—CH($C_{1-4}$-alkyl)-, $C_{1-4}$-alkyl-OOC—$CH_2$—, benzyl-OOC—$CH_2$—, and where

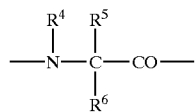

is

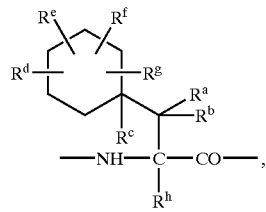

($R^a$, $R^b$=H, cyclohexyl- or $C_{1-4}$-alkyl-) ($R^c$, $R^d$, $R^e$, $R^f$, $R^g$, $R^h$=H— or $C_{1-4}$-alkyl-, where the $CH_2$ groups of the ring can be mono- or disubstituted),

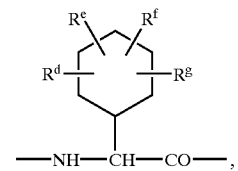

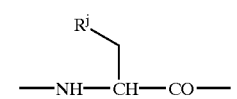

($R^i$=phenyl- or cyclohexyl-)

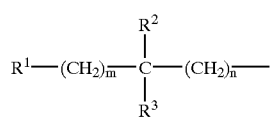

($R^j$=cyclopentyl-, cycloheptyl-, 1-adamantyl-, 1-norbornyl-, 1-bicyclo[2.2.2]octyl-, neopentyl-, tert-butyl-, diisopropylmethyl- or 1-(1,4-cyclohexadienyl-))
where this building block preferably has the D configuration,
l is 0 or 1 and
R is H— or $CH_3$—.

Further interesting intermediates are the compounds of the formula

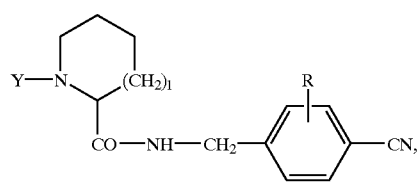

where l and R have the meanings specified in claim 1, and Y is an N protective group, an N-terminally protected or unprotected amino acid or H—.

Preferred compounds of the formula III are those where Y is Boc- , Boc-Cha- , H-Cha-, Boc-Chg-, H-Chg or H, l is 0 or 1 and R is H or $CH_3$.

The following substances are particularly preferred:
1. HOOC—$CH_2$-(D)-Cha-Pyr-NH-4-amb
2. HOOC-$(CH_2)_2$-(D)-Cha-Pyr-NH-4-amb
3. (HOOC—$CH_2)_2$CH-(D)-Cha-Pyr-NH-4-amb
4. (HO—$CH_2)_2$CH-(D)-Cha-Pyr-NH-4-amb
5. HOOC—$CH_2$-CH(COOH)-(D)-Cha-Pyr-NH-4-amb
6. HOOC—$CH_2$-(D)-Chg-Pyr-NH-4-amb
7. HOOC—$CH_2$-(D)-($\alpha$-Me)Cha-Pyr-NH-4-amb
8. HOOC—$CH_2$-(D,L)-(1-Me)Cha-Pyr-NH-4-amb
9. HOOC—$CH_2$-(D,L)-($\beta,\beta$-$Me_2$)Cha-Pyr-NH-4-amb
10. HOOC—$CH_2$-(D,L)-(trans 4-Me)Cha-Pyr-NH-4-amb
11. HOOC—$CH_2$-(D,L)-cycloheptylalanine-Pyr-NH-4-amb
12. HOOC—$CH_2$-(D,L)-1-adamantylalanine-Pyr-NH-4-amb
13. HOOC—$CH_2$-(D,L)-2-norbornylglycine-Pyr-NH-4-amb
14. HOOC—$CH_2$-(D,L)-(3,3-$Me_2$)Cha-Pyr-NH-4-amb
15. HOOC—$CH_2$-(D)-tert-butylalanine-Pyr-NH-4-amb
16. HOOC—$CH_2$-(D,L)(1,4-cyclohexadien-1-yl)alanine-Pyr-NH-4-amb
17. HOOC—$CH_2$-(D)-Cha-Dep-NH-4-amb
18. HOOC—$CH_2$-(D)-Chg-Dep-NH-4-amb
19. HOOC—$CH_2$-(D,L)-Dch-Pyr-NH-4-amb The abbreviations used here and in the examples are as follows:
amb=amidinobenzyl
Boc=tert-butyloxycarbonyl
Cha=cyclohexylalanine
Chea=cycloheptylalanine
Chg=cyclohexylglycine
Dch=dicyclohexylalanine
Dpa=diphenylalanine
Me=methyl
Pyr=3,4-dehydroproline
Dep=4,5-dehydropipecolic acid In the case where —$NR^4$—$CR^5R^6$—CO— is a cyclohexylalanine residue, the individual carbon atoms are designated as follows:

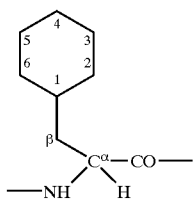

The compounds of the formula I can exist as such or in the form of their salts with physiologically tolerated acids. Examples of such acids are: hydrochloric acid, citric acid, tartaric acid, lactic acid, phosphoric acid, methanesulfonic acid, acetic acid, formic acid, maleic acid, fumaric acid, succinic acid, hydroxysuccinic acid, sulfuric acid, glutaric acid, aspartic acid, pyruvic acid, benzoic acid, glucuronic acid, oxalic acid, ascorbic acid and acetylglycine.

The novel compounds of the formula I can be employed for the following indications:
diseases whose pathogenetic mechanism derives directly or indirectly from the proteolytic effect of thrombin,
diseases whose pathogenetic mechanism derives from thrombin-dependent activation of receptors and signal transduction,
diseases associated with stimulation [e.g. by PAI-1, PDGF (platelet derived growth factor), P-selectin, ICAM-1, tissue factor] or inhibition (e.g. NO synthesis in smooth muscle cells) of the expression of genes in body cells,
diseases deriving from the mitogenic effect of thrombin,
diseases deriving from a thrombin-dependent change in the contractility and permeability of epithelial cells (e.g. vascular endothelial cells),
thrombin-dependent thromboembolic events such as deep vein thrombosis, pulmonary embolism, myocardial or cerebral infarct, atrial fibrillation, bypass occlusion,
disseminated intravascular coagulation (DIC),
reocclusion and for reducing the reperfusion time on comedication with thrombolytics such as streptokinase, urokinase, prourokinase, t-PA, APSAC, plasminogen activators from the salivary glands of animals, and the recombinant and mutated forms of all these substances,
the occurrence of early reocclusion and late restenosis after PTCA,
the thrombin-dependent proliferation of smooth muscle cells,
the accumulation of active thrombin in the CNS (e.g. in Alzheimer's disease),
tumor growth, and to prevent adhesion and metastasis of tumor cells.

The novel compounds can be used in particular for the therapy and prophylaxis of thrombin-dependent thromboembolic events such as deep vein thromboses, pulmonary embolisms, myocardial or cerebral infarcts and unstable angina, also for the therapy of disseminated intravascular coagulation (DIC). They are furthermore suitable for combination therapy with thrombolytics such as streptokinase, urokinase, prourokinase, t-PA, APSAC and other plasminogen activators to shorten the reperfusion time and extend the reocclusion time.

Further preferred areas of use are to prevent thrombin-dependent early reocclusion and late restenosis after percutaneous transluminal coronary angioplasty, to prevent thrombin-produced proliferation of smooth muscle cells, to prevent accumulation of active thrombin in the CNS (e.g. in Alzheimer's disease), to control tumors and to prevent mechanisms which lead to adhesion and metastasis of tumor cells.

The novel compounds can also be used for coating artificial surfaces such as hemodialysis membranes and the tubing systems and lines necessary therefor, and of oxygenators in extravascular circulation, stents and heart valves.

The novel compounds can furthermore be employed for diseases whose pathogenetic mechanism derives directly or indirectly from the proteolytic effect of kininogenases, especially kallikrein, e.g. in inflammatory diseases such as asthma, pancreatitis, rhinitis, arthritis, urticaria and other internal inflammatory diseases.

The particular advantage of the novel compounds is that they show, owing to replacement of proline by 3,4-dehydroproline and by replacement of pipecolic acid by 4,5-dehydropipecolic acid, an improved pharmacological effect and are therefore to be distinguished from the compounds described in WO 94/29336.

The compounds according to the invention can be administered in a conventional way orally or parenterally (subcutaneously, intravenously, intramuscularly, intraperitoneally, rectally). Administration can also take place with vapors or sprays through the nasopharyngeal space.

The dosage depends on the age, condition and weight of the patient and on the mode of administration. As a rule, the daily dose of active substance per person is about 10–2000 mg on oral administration and about 1–200 mg on parenteral administration. This dose can be given in 2 to 4 single doses or once a day as depot form.

The novel compounds can be used in conventional solid or liquid pharmaceutical forms, e.g. as uncoated or (film-) coated tablets, capsules, powders, granules, suppositories, solutions, ointments, creams or sprays. These are produced in a conventional manner. The active substances can for this purpose be mixed with conventional pharmaceutical auxiliaries such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain from 0.1 to 99% by eight of active substance.

MODE(S) FOR CARRYING OUT THE INVENTION

The compounds of the formula I can be prepared as shown in schemes I–III,
where A is

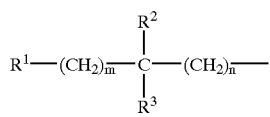

B is

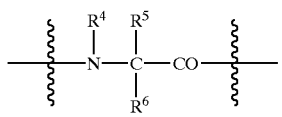

C is

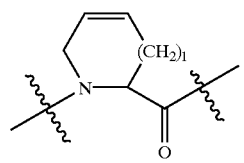

D is

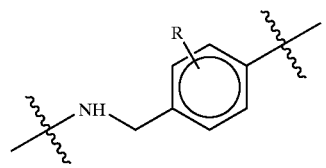

and E has the meaning indicated in the schemes. The radicals R, $R^1$, $R^2$, $R^3$, $R^4$, $R^5$ and $R^6$, and l, m and n have the abovementioned meanings.

Building blocks A, B, C and D are preferably assembled separately beforehand and employed in suitably protected form (see scheme I–III).

The compounds of the formula I can be prepared starting from appropriately protected building blocks A, B, C, D and E as shown in scheme I–III.

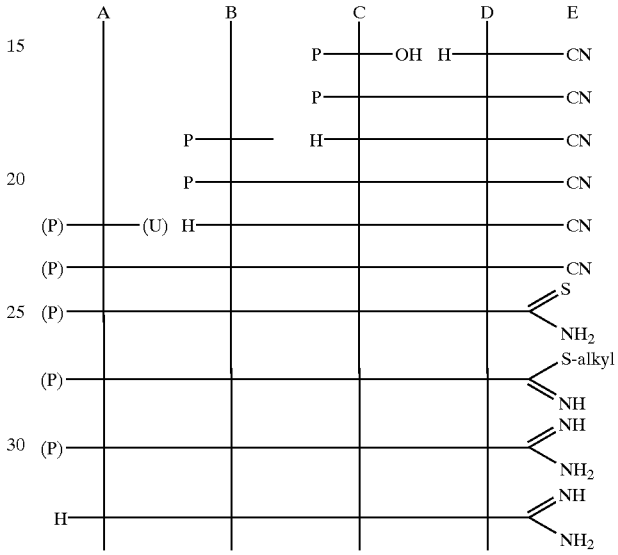

(P = protective group, (P) = protective group or H, (U) = leaving group or, where appropriate, aldehyde or ketone, see following text)

Scheme I describes linear assemblage of the molecule I by coupling the amine H-D-CN to the N-protected amino acid P-C-OH to give P-C-D-N, eliminating the N-terminal protective group to give M-C-D-CN, coupling to the N-protected amino acid P-B-OH to give P-B-C-D-CN, eliminating the protective group P to give H-B-C-D-CN, subsequently alkylating with the unprotected or protected (P)-A-U building block (U=leaving group) or reductively aminating with (P)-A'-U (U=aldehyde, ketone) or Michael addition with a suitable (P)-A''-C=C derivative to give (P)-A-B-C-D-CN. Conversion of the nitrile functionality into the amidine group takes place either by the classical Pinner synthesis (R. Boder, D. G. Neilson, Chem. Rev. 61 (1962) 179) or by a modified Pinner synthesis which proceeds via imino thioester salts as intermediate (H. Vieweg et al., Pharmazie 39 (1984) 226) or directly by the method of A. Eschenmoser, Helv. Chimica Acta 69 (1986) 1224. Subsequently the protective groups still present in the molecule are eliminated, preferably by acid hydrolysis.

If building block D is incorporated as H-D-$CONH_2$ into the synthesis, dehydration of the amide to the nitrile functionality takes place on one of the protected intermediates.

Scheme II

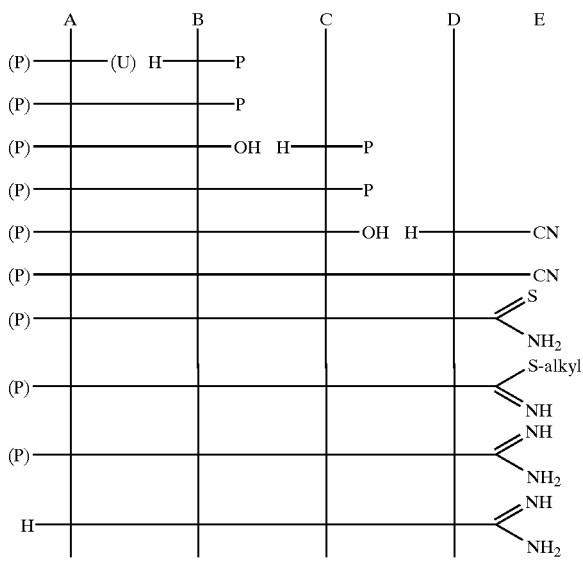

Scheme II describes linear assemblage of the molecule I by alkylation, reductive amination or Michael addition of H-B-P onto appropriately suitable unprotected or protected A building blocks to give (P)-A-B-P, elimination of the C-terminal protective group to give (P)-A-B-OH, coupling to H-C-P to give (P)-A-B-C-P, elimination of the C-terminal protective group to give (P)-A-B-C-OH, coupling to H-D-CN to give (P)-A-B-C-D-CN and reaction of this intermediate to give the final product as in scheme I.

Where compounds (P)-A-B-P still have a free NH functionality on B, this must be provided with a suitable protective group before elimination of the C-terminal protective group. The protective groups used in each case must be orthogonal to one another.

As an alternative to the H-D-CN building block, it is also possible to employ H-D-CONH$_2$, H-D-C(NH)NH$_2$, H-D-C(NP)NH$_2$, H-D-C(NP)NHP, with the coupled intermediate (P)-A-B-C-D-CONH$_2$ in the first case being dehydrated to (P)-A-B-C-D-CN.

Scheme III

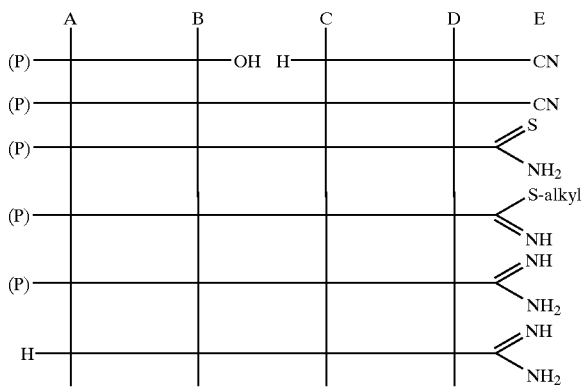

Scheme III describes a very efficient way for preparing compounds I by a convergent synthesis. The appropriately protected building blocks (P)-A-B-OH and H-C-D-CN are coupled together, and the resulting intermediate (P)-A-B-C-D-CN is reacted to give the final product as in scheme I.

The N-terminal protective groups employed are Boc, Cbz or Fmoc, preferably Boc, and the C-terminal protective groups are methyl, tert-butyl and benzyl. If a plurality of protective groups is present in the molecule, they must be orthogonal to one another if they are not to be eliminated simultaneously. If the intermediates contain building block C, the Cbz and benzyl protective groups are unsuitable.

The required coupling reactions and the other reactions for introducing and eliminating protective groups are carried out under standard conditions of peptide chemistry (see M. Bodanszky, A. Bodanszky "The Practice of Peptide Synthesis", 2nd Edition, Springer Verlag Heidelberg, 1994).

Boc protective groups are eliminated using dioxane/HCl or TFA/DCM, and Cbz protective groups are eliminated by hydrogenolysis or with HF. Hydrolysis of ester functionalities takes place with LiOH in an alcoholic solvent or in dioxane/water. TFA is used to cleave t-butyl esters.

The reactions were checked by TLC, normally using the following mobile phases:

| A. DCM/MeOH | 95:5 |
|---|---|
| B. DCM/MeOH | 9:1 |
| C. DCM/MeOH | 8:2 |
| D. DCM/MeOH/50% HOAc | 40:10:5 |
| E. DCM/MeOH/50% HOAc | 35:15:5 |

Where separations by column chromatography are mentioned, these were separations on silica gel using the abovementioned mobile phases.

Reversed phase HPLC separations were carried out with acetonitrile/water and HOAc buffer.

The Starting Compounds can be Prepared by the Following Methods:

Examples of building blocks A employed for the alkylation are tert-butyl α-bromoacetate, tert-butyl β-bromopropionate, tert-butyl α-bromopropionate, tert-butyl γ-bromobutyrate, tert-butyl α-bromobutyrate, THP-protected bromoethanol, THP-protected γ-bromopropanol, α-bromo-γ-butyrolactone, for the reductive amination are dihydroxyacetone, di-tert-butyl acetonedicarboxylate, and for the Michael addition are tert-butyl acrylate, tert-butyl methacrylate, tert-butyl fumarate. Those of said tert-butyl esters which cannot be purchased are prepared by methods similar to G. Uray, W. Lindner, Tetrahedron 44 1988 4357–4362 corresponding carboxylic acids.

B Building Blocks:

A wide variety of possibilities is available in the literature for the general and specific synthesis of amino acids. A review thereof is provided by, inter alia, Houben-Weyl, Volume E16d/Part 1, pages 406 et seq.

Precursors which were frequently employed were benzophenone imine acetic acid ethyl ester, diethyl acetamidomalonate and ethyl isonitrileacetate.

Various glycine and alanine derivatives were prepared, for example, starting from ethyl isonitrileacetate and an appropriate ketone or aldehyde (see H.-J. Prätorius, J. Flossdorf, M.-R. Kula Chem. Ber. 108 (1975) 3079).

The syntheses of 2-norbornylglycine, adamantylalanine, β-methylcyclohexylalanine, 4-isopropyl-1-cyclohexylalanine, 4-methyl-1-cyclohexylalanine and 4-methyl-1-cyclohexylglycine were carried out via the corresponding ethyl 2-formylaminoacrylates (U. Schöllkopf and R. Meyer, Liebigs Ann. Chem. 1977, 1174) starting from ethyl isocyanoacetate with the relevant carbonyl compounds 2-norbornanone, 1-formyladamantane, 1-formyl-1- methylcyclohexane, 1-formyl-4-isopropylcyclohexane, 1-formyl-4-methylcyclohexane and 4-methylcyclohexanone by the following general methods:

General Method for Synthesizing Ethyl 2-Formylaminoacrylates

A solution of 100 mmol of ethyl isocyanoacetate in 50 ml of THF is added dropwise to 100 mmol of potassium tert-butoxide in 150 ml of THF at 0 to −10° C. After 15 min, at the same temperature 100 mmol of the appropriate carbonyl compound in 50 ml of THF are added, the reaction mixture is allowed slowly to rise to RT, and the solvent is stripped off in a rotary evaporator. The residue is mixed with 50 ml of water, 100 ml of acetic acid and 100 ml of DCM, and the product is extracted with DCM. The DCM phase is dried over $Na_2SO_4$, and the solvent is stripped off in a rotary evaporator. The products result almost pure but can, if necessary, be purified further by column chromatography on silica gel (mobile phases: ether/petroleum ether mixtures).

General method for amino acid hydrochlorides starting from the ethyl 2-formylaminoacrylates 100 mmol of the ethyl 2-formylaminoacrylates are hydrogenated with Pd/C (10%) and hydrogen in 200 ml of glacial acetic acid until the reaction is complete. The catalyst is then filtered off, the acetic acid is stripped off as far as possible in a rotary evaporator, and the residue is refluxed in 200 ml of 50% concentrated hydrochloric acid for 5 h. The hydrochloric acid is stripped off in a rotary evaporator, and the product is dried at 50° C. under reduced pressure and then washed several times with ether. The hydrochlorides result as pale colored crystals.

26.6 g of 2-norbornylglycine hydrochloride were obtained starting from 16.5 g (150 mmol) of 2-norbornanone. 26.0 g of adamantylalanine hydrochloride were obtained starting from 19.7 g (120 mmol) of 1-formyladamantane. 16.6 g of γ-methylcyclohexylalanine hydrochloride were obtained starting from 12.6 g (100 mmol) of 1-formyl-1-methylcyclohexane. 25.9 g of 4-methylcyclohexylglycine hydrochloride were obtained starting from 16.8 g (150 mmol) of 4-methylcyclohexanone.

18 g of trans-4-methyl-1-cyclohexylalanine hydrochloride were obtained starting from 15 g of trans-1-formyl-4-methylcyclo-hexane.

10 g of 3,3-dimethyl-1-cyclohexylalanine hydrochloride were obtained starting from 9 g of 3,3-dimethyl-1-formylcyclohexane.

The aldehyde 1-formyl-3,3-dimethylcyclohexane required for the synthesis is prepared by a method based on those of Moskal and Leusen (Rec. Trav. Chim. Pays-Bas 106 (1987) 137–141:

A solution of n-butyllithium in n-hexane (72 ml, 115 mmol) was added dropwise over the course of 10 min to a stirred solution of diethyl isocyanomethylphosphonate (17 ml, 105 mmol) in 280 ml of anhydrous diethyl ether at −60° C. The resulting suspension was then stirred at −60° C. for 15 min and, over the course of 10 min, a solution of 3,3-dimethylcyclohexanone (13 g, 105 mmol) in 100 ml of anhydrous diethyl ether was added, keeping the temperature below −45° C. The reaction mixture was allowed to reach 0° C. and, after stirring at this temperature for 90 min, 150–200 ml of 38% strength aqueous hydrochloric acid were cautiously added. The mixture was vigorously stirred at room temperature for 15 h to complete the hydrolysis. The organic phase was separated off and washed with 200 ml each of water, saturated sodium bicarbonate solution and saturated sodium chloride solution. It was dried over magnesium sulfate, filtered and concentrated in a rotary evaporator in order to remove the solvent. The resulting residue as employed without further purification as starting material for synthesizing the amino acid.

Boc-(D)-α-methyl-cyclohexylalanine:

3.4 g (12.2 mmol) of Boc-(D)-α-methyl-Phe-OH were hydrogenated in 100 ml of MeOH in the presence of 250 mg of 5% Rh on $Al_2O_3$ under 10 bar of hydrogen at 50° C. for 24 h. Filtration and stripping off the solvent resulted in 2.8 g of Boc-(D)-α-methyl-Cha-OH.

$^1$H-NMR (DMSO-d$^6$, δ in ppm): 12 (very broad signal, COOH); 1.7–0.8 (25 H; 1.35 (s, Boc), 1.30 (s, Me))

Boc-(3-Ph)-Pro-OH was synthesized by a method similar to that of J. Y. L. Chung et al. (J. Y. L. Chung et al. J. Org. Chem. 1990, 55, 270).

Preparation of Boc-(D,L)-Dch-OH:

Boc-(D,L)-Dpa-OH (1 mmol) was hydrogenated in 12 ml of MeOH together with catalytic amounts of 5% Rh/$Al_2O_3$ under 5 bar. Filtration and removal of the solvent under reduced pressure resulted in the product in quantitative yield.

Preparation of H-(D,L)-Chea-OH:

4.0 g of cycloheptylmethyl methanesulfonate (19.39 mmol), prepared from cycloheptylmethanol and methanesulfonyl chloride, were refluxed together with 4.9 g of benzophenone imine glycine ethyl ester (18.47 mmol), 8.9 g of dry, finely powdered potassium carbonate (64.65 mmol) and 1 g of tetrabutylammonium bromide (3 mmol) in 50 ml of dry acetonitrile under an inert gas atmosphere for 10 h. The potassium carbonate was then filtered off, the filtrate was evaporated to dryness, and the crude product was hydrolyzed directly with 20 ml of 2N hydrochloric acid in 40 ml of ethanol, stirring at RT for 1.5 h. The reaction solution was diluted and then benzophenone was extracted with ethyl acetate in the acidic range, and subsequently H-(D,L)-Chea-OEt was extracted with DCM in the alkaline range (pH=9), and the solution was dried over magnesium sulfate and concentrated in a rotary evaporator. Yield 3.7 g=95% of theory.

D-(1,4-Cyclohexadien-1-yl)ala-OH was prepared by the method of G. Zivilichovsky, V. Gurvich J. Chem. Soc., Perkin Trans I 19 (1995) 2509–15.

H-(D,L)-β,β-Me$_2$Cha-OH was prepared by the method of U. Schöllkopf, R. Meyer, L. Ann. Chem. (1977) 1174–82.

Said amino acids were converted with di-tert-butyl dicarbonate in water/dioxane by conventional methods into the Boc-protected form in each case and subsequently recrystallized from ethyl acetate/hexane mixtures or purified by column chromatography on silica gel (mobile phases: ethyl acetate/petroleum ether mixtures.

The Boc-protected amino acids were employed as B building blocks as shown in scheme I.

Said amino acids as B building blocks were also in some cases converted into the corresponding benzyl esters and linked to the appropriately protected A building blocks. In the case of compounds with an N-H functionality which was still free, this was subsequently protected with a Boc group, the benzyl ester group was removed by hydrogenation, and the building block A-B-OH was purified by crystallization, salt precipitation or column chromatography. This route is described by way of example for tBuOOC—CH$_2$-(Boc)(D) Cha below.

Synthesis of (D)-cyclohexylalanine Benzyl Ester:

A suspension of 100 g (481 mmol) of D-cyclohexylalanine hydrochloride, 104 g (962 mmol) of benzyl alcohol and 110 g (577 mmol) of p-toluenesulfonic acid monohydrate in 2200 ml of toluene was slowly heated to reflux with a water separator. Evolution of hydrogen chloride and dissolving of the suspension to give a clear solution were observed in the temperature range 80–90° C. When no further water separated out (about 4 h), 500 ml of toluene were distilled out, the reaction mixture was allowed to cool overnight, and the resulting residue was filtered off and washed twice with 1000 ml of hexane each time. The resulting residue (195 g) was then suspended in 2000 ml of dichloromethane and, after addition of 1000 ml of water, adjusted to pH 9–9.5 by gradual addition of 50% strength sodium hydroxide solution while stirring. The organic phase was separated off, washed twice with 500 ml of water each time, dried over sodium sulfate and filtered to remove desiccant, and concentration of the filtrate resulted in 115 g (94%) of the product as pale oil.

N-(tert-butyloxycarbonylmethyl)-(D)-cyclohexylalanine Benzyl Ester:

115 g (440 mmol) of (D)-cyclohexylalanine benzyl ester were dissolved in 2000 ml of acetonitrile and, at room temperature, 608 g (4.40 mol) of potassium carbonate and 94 g (484 mmol) of tert-butyl bromoacetate were added, and the mixture was stirred at this temperature for 3 days. The carbonate was filtered off, washing with acetonitrile, the mother liquor was concentrated (30° C., 20 mbar), the residue was taken up in 1000 ml of methyl tert-butyl ether, and the organic phase was extracted with 5% strength citric acid and saturated sodium bicarbonate solution. The organic phase was dried over sodium sulfate, filtered to remove desiccant and concentrated, and the resulting oil (168 g) was employed directly in the next reaction.

N-Boc-N-(tert-butyloxycarbonylmethyl)-(D)-cyclohexylalanine Benzyl Ester:

The oil (168 g, 447 mmol) obtained in the previous synthesis was dissolved in 1400 ml of acetonitrole and, after addition of 618 g (4.47 mmol) of potassium carbonate powder and 107 g (492 mmol) of di-tert-butyl dicarbonate, stirred at room temperature for 6 days. The potassium carbonate was filtered off with suction, washing with about 1000 ml of acetonitrile, and the filtrate was concentrated. 230 g of the required product were obtained. N-Boc-N-(tert-butyloxycarbonylmethyl)-(D)-cyclohexylalanine cyclohexylammonium salt:

115 g of N-Boc-N-(tert-butyloxycarbonylmethyl)-(D)-cyclohexyl-alanine benzyl ester were dissolved in 1000 ml of pure ethanol and hydrogenated in the presence of 9 g of 10% Pd on active carbon under hydrogen at atmospheric pressure at 25–30° C. for 2 h. Filtration and removal of the solvent in a rotary evaporator resulted in 100 g (260 mmol) of a yellow oil which was taken up in 1600 ml of acetone and heated to reflux. The heating bath was removed, and a solution of 27 g (273 mmol) of cyclohexylamine in acetone was quickly added through a dropping funnel. The required salt crystallized out on cooling the reaction mixture to room temperature. The solid was filtered off, washed with 200 ml of acetone and, for final purification, recrystallized once more from acetone. Drying of the residue in a vacuum of about 30° C. resulted in 70.2 g of the required salt as white powder.

(L)-3,4-Dehydroproline employed as C building block can be purchased, and (D,L)-4,5-dehydropipecolic acid can be prepared J. Org. Chem. 25 (1960) 489 or C. Herdeis, W. Engel Arch. Pharm. 326 (1993) 297 and subsequently converted with $Boc_2O$ into Boc-(D,L)-Dep-OH.

Synthesis of the D building blocks is described in DE 444 33 90.

EXAMPLE 1

N-Hydroxycarbonylmethylene-(D)-cyclohexylalanyl-3,4-dehydroprolyl (4-Amidino) benzylamide Boc-3,4-dehydroprolyl-4-cyanobenzylamide:

Boc-3,4-dehydroproline (4.7 g, 22.0 mmol) and 4-cyanobenzylamine (4.1 g, 24.2 mmol; DE 444 33 90) were dissolved in dichloro-methane (25 ml). The solution was cooled to 0° C., and ethyl diisopropylamine (26.4 ml, 154 mmol) was added. Subsequently, 50% strength propanephosphonic anhydride in ethyl acetate (23.3 ml, 110 mmol) was slowly added dropwise. The mixture was stirred at 0° C. for 1 h and at room temperature for 30 min and then diluted with dichloromethane and washed with dilute sodium bisulfate solution (3×), dilute sodium bicarbonate solution (3×) and saturated sodium chloride solution. Drying over sodium sulfate was followed by concentration under waterpump vacuum. 7.47 g of crude product were obtained.

3,4-Dehydroprolyl-4-cyanobenzylamide:

The Boc-3,4-dehydroprolyl 4-cyanobenzylamide crude product (7.47 g) obtained in the previous experiment was dissolved in dichloromethane (88 ml) and ethereal hydrochloric acid (88 ml, 5 M) was added. The mixture was then stirred at room temperature for 1.5 h. The solvent was distilled off under waterpump vacuum. The residue was twice mixed with dichloromethane and the solvent distilled off under waterpump vacuum. It was then extracted by stirring twice with diethyl ether. 5.32 g of crude product were obtained.

N-(tert-Butoxycarbonylmethylene)-(N-BOC)-(D)-cyclohexylalanyl-3,4-dehydroprolyl 4-Cyanobenzylamide tBuOOC—$CH_2$-(Boc)-(D)-Cha-OH (7.59 g, 19.68 mmol) and H-Pyr-4-cyanobenzylamide (5.19 g, 19.68 mmol) were dissolved in dichloromethane (100 ml), and ethyldiisopropylamine (12.72 g, 98.4 mmol) was added. The solution was cooled to 0° C., and 50% strength propanephosphonic anhydride in ethyl acetate (20 ml) was added dropwise over the course of 20 min and, after stirring at 0–10° C. for 3 h, the mixture was diluted with dichloromethane (100 ml) and washed with 10% strength sodium bisulfate solution (3×), saturated sodium bicarbonate solution (2×) and water. Drying over sodium sulfate was followed by removal of the solvent by distillation under waterpump vacuum. 13.28 g of a pale brownish oil were obtained.

N-(tert-Butoxycarbonylmethylene)-(N-Boc)-(D)-cyclohexylalanyl-3,4-dehydroprolyl 4-Aminothiocarbonylbenzylamide The t-BuOOC—$CH_2$-(Boc)-(D)-Cha-Pyr 4-cyanobenzylamide (13.28 g) crude product obtained in the previous experiment was dissolved in pyridine (70 ml) and triethylamine (12 ml), and the solution was cooled to 0° C. and saturated with hydrogen sulfide (solution became green in color). It was then stirred at room temperature for 48 h. Excess hydrogen sulfide was displaced with nitrogen, and the solvent was dissolved off under waterpump vacuum. The residue was dissolved in diethyl ether and washed 3× with 20% strength sodium bisulfate solution, saturated sodium bicarbonate solution (2×) and water. Drying over sodium sulfate was followed by removal of the solvent by distillation under waterpump vacuum. The crude product (14.3 g) was purified by flash chromatography (silica gel, gradient from dichloromethane to dichloromethane:methanol=50:1). Yield: 13.3 g (contains small amount of solvent).

N-(tert-Butoxycarbonylmethylene)-(N-Boc)-(D)-cyclohexylalanyl-3,4-dehydroprolyl 4-S-methylimiinocarbonylbenzylamide Methyl iodide (7.97 ml, 126.90 mmol) was added to the t-BuOOC—CH$_2$-(Boc)-(D)-Cha-Pyr-aminothiocarbonyl-benzylamide (13.3 g) obtained in the previous experiment in dichloromethane (135 ml). After stirring at room temperature for 24 h, the solvent was distilled off under waterpump vacuum. 15.73 g of a pale yellowish oil were obtained.

N-(tert-Butoxycarbonylmethylene)-(N-Boc)-(D)-cyclohexylalanyl-3,4-dehydroprolyl 4-Amidinobenzylamide The t-BuOOC—CH$_2$-(Boc)-(D)-Cha-Pyr 4-S-methyliminocarbonyl-benzylamide hydroiodide (15.73 g) crude product obtained from the previous experiment was dissolved in acetonitrile (1290 ml), and ammonium acetate (3.25 g, 42.3 mmol) was added. The mixture was then heated at 50° C. for 1.5 h and, after concentration under waterpump vacuum, dichloromethane was added. The precipitated salts were filtered off, and the filtrate was concentrated under waterpump vacuum. 15.17 g of a yellowish foam were obtained. The crude product was converted into the acetate on an ion exchanger (Fluka, Order No. 00402, acetate on polymeric support). Yield: 13.3 g.

N-(Hydroxycarbonylmethylene)-(D)-cyclohexylalanyl-3,4-dehydro-prolyl (4-Amidino) benzylamide t-BuOOC—CH$_2$-(Boc)-(D)-Cha-Pyr 4-amidinobenzylamide hydroacetate (13.3 g) was dissolved in dichloromethane (200 ml), and ethereal HCl (45 ml) was added. Stirring at room temperature for 2 h was followed by evaporation to dryness under waterpump vacuum. The residue was twice mixed with dichloromethane and the solvent distilled off under waterpump vacuum. 11.6 g of crude product were obtained.

Part of the crude product (3 g) was converted into the acetate on an ion exchanger (Fluka, Order No. 00402, acetate on polymeric support). The resulting product (2.9 g) was purified by flash chromatography (silica gel, gradient from dichloromethane:methanol=4:1 via dichloromethane:methanol:50% strength acetic acid=40:10:2 to dichloromethane:methanol:50% strength acetic acid=35:15:5). A yellowish oil was obtained and was dissolved in water. After filtration, the filtrate was freeze-dried. Yield: 2.13 g of a colorless solid. FAB-MS (M+H$^+$): 456.

The following were prepared in a similar way to Example 1:

2. N-(Hydroxycarbonylmethylene)-(D)-cyclohexylglycyl-3,4-dehydroprolyl (4-amidino) benzylamide:
FAB-MS (M+H$^+$): 442

3. N-(Hydroxycarbonylmethylene)-(D,L)-cycloheptylalanyl-3,4-dehydroprolyl (4-amidino) benzylamide:
FAB-MS (M+H$^+$): 470

4. N-(Hydroxycarbonylmethylene)-(D)-tert-butylalanyl-3,4-dehydroprolyl (4-amidino)benzylamide:
FAB-MS (M+H$^+$): 430

5. N-(Hydroxycarbonylmethylene)-(D)-cyclohexylalanyl-4,5-dehydropipecolyl (4-amidino) benzylamide:
FAB-MS (M+H$^+$): 470

The antithrombotic effect of the novel compounds was shown in the arteriovenous shunt in rats. In this experiment, a glass capillary in an arteriovenous shunt acts as artificial thrombogenic surface and initiates thrombosis. The anesthetized (urethane 25%, 2×8 mg/kg i.p.) rat is fixed supine on a temperature-controlled (37° C.) stage. The right carotid artery and jugular vein are exposed and short polyethylene catheters (Portex, PE 50) are implanted in them, filled with physiol. NaCl solution and clamped. The free ends of the catheters are connected by a glass capillary with an internal diameter of 1.0 mm and a length of 20.0 mm which acts as thrombogenic surface. The test substance can be administered i.v., s.c., orally or by infusion. After the required incubation time with the test substance or solvent (control), the shunt is opened by removing the clamps. The blood flow through the shunt leads to a rapid rise in its temperature, which is measured at the center of the glass capillary. The increase from room temperature to body temperature indicates the patency of the shunt. The temperature is recorded continuously until the shunt becomes blocked. In addition, blood samples are taken for determination of the anti-FIIa activity in plasma when the shunt is opened and at the end of the experiment.

Pharmacokinetics and Coagulation Parameters in Dogs

The test substances are dissolved in isotonic saline immediately before administration to conscious mongrel dogs. The volumes administered are 0.1 ml/kg for the intravenous bolus injection and 1 ml/kg for oral administration by gavage. Samples of venous blood (2 ml) in citrated tubes are taken before and 5, 10, 20, 30, 45, 60, 90, 120, 180, 240, 300 and 360 min (if required after 420, 480 min and 24 h) after intravenous administration of 1.0 mg/kg, or before and 10, 20, 30, 60, 120, 180, 240, 300, 360, 480 min and 24 h after oral administration of 4.64 mg/kg. Immediately after sampling, the ecarin time (ECT=ecarin clotting time) is determined on the whole blood. After preparation of the plasma by centrifugation, the plasma thrombin time and the activated partial thromboplastin time (APTT) are determined using a coagulometer.

Also determined are the anti-FIIa activity (ATU/ml) and the concentration of the substance through its anti-F IIa activity in the plasma by a chromogenic (S-2238) thrombin assay, employing calibration plots with r-hirudin and the test substance.

The plasma concentration of the test substance is the basis for calculating the pharmacokinetic parameters:time of the maximum plasma concentration (T max), maximum plasma concentration; 20 plasma half-life $T_{0.5}$; area under the curve (AUC); absorbed fraction of the test substance (F).

Coagulation Parameters:

Ecarin time (ECT=ecarin clotting time): 100 µl of citrate-treated blood are incubated in a coagulometer (CL 8, ball type, Bender & Hobein, Munich, FRG) at 37° C. for 2 min. After addition of 100 µl of prewarmed (37° C.) ecarin reagent (Pentapharm) the time until a fibrin clot forms is determined.

Activated thromboplastin time (APTT): 50 µl of citrate-treated plasma and 50 µl of the PTT reagent (Pathrombin, Behring) are mixed and incubated in a coagulometer (CL 8, ball type, Bender & Hobein, Munich, FRG) at 37° C. for 2 min. After addition of 50 µl of prewarmed (37° C.) calcium chloride, the time until a fibrin clot forms is determined.

Thrombin time (TT): 100 µl of citrate-treated plasma are incubated in a coagulometer (CL 8, ball type, Bender & Hobein, Munich, FRG) at 37° C. for 2 min. After addition of 100 μl of prewarmed (37° C.) thrombin reagent (Boehringer Mannheim), the time until a fibrin clot forms is determined.

The novel compounds showed a good effect in these tests.

We claim:

1. A compound of the formula I

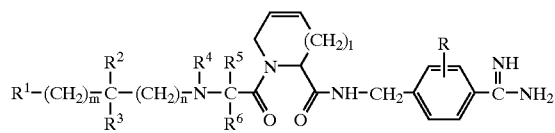

(I)

wherein l is 0 or 1, m is 0, 1 or 2, n is 0, 1 or 2,

R is hydrogen or $C_{1-4}$-alkyl, $R^1$ is HOOC—, $C_{1-6}$-alkyl-OOC, benzyl-OOC or hydroxyl, $R^2$ is hydrogen, $C_{1-4}$-alkyl or $R^1$—$(CH_2)_m$, $R^3$ is hydrogen or $C_{1-4}$-alkyl which is unsubstituted or substituted by hydroxyl or COOH, $R^4$ is hydrogen, $C_{1-4}$-alkyl, HOOC—$C_{1-4}$-alkylene, $R^5$ is $C_{1-8}$-alkyl, cycloalkyl-$(CR^8R^9)_r$, (r=0 or 1, $R^8$, $R^9$=hydrogen, cycloalkyl or $C_{1-4}$-alkyl), wherein up to four $CH_2$ groups of the cycloalkyl radical may be replaced, independently from one another, by $CR^{10}R^{11}$ ($R^{10}$=hydrogen or $C_{1-4}$-alkyl, $R^{11}$=$C_{1-4}$-alkyl) and/or the CH group in the cycloalkyl radical which is bonded to $CR^8R^9$ may be replaced by $CR^{12}$ ($R^{12}$=$C_{1-4}$-alkyl), and/or one or two C—C single bond(s) of the cycloalkyl ring may be replaced by a C=C double bond, $R^6$ is hydrogen, $C_{1-4}$-alkyl, or $R^4$ and $R^5$ are together $CH_2$—$CH_2$—$CH(R^7)$, ($R^7$= hydrogen, phenyl or cyclohexyl), or $R^2$ and $R^5$ are together $CH_2$—$CH_2$ or $CH_2$—$CH_2$—$CH_2$, in which one hydrogen atom may be replaced by $C_{1-4}$-alkyl, phenyl or cycloalkyl, or a salt thereof.

2. The compound of the formula I defined in claim 1, wherein the amino acid moiety represented by —$NR^4$—$CR^5R^6$—CO— is in the D configuration.

3. The compound of the formula I defined in claim 1, wherein the 3,4-dehydroproline moiety or 4,5-dehydropipecoline moiety is in the L configuration.

4. The compound of the formula I defined in claim 1, wherein the moiety $R^1$—$(CH_2)_m$—$CR^2R^3$—$(CH_2)_n$ represents one of the following groups: HOOC—$(CH_2)_t$ (t=1, 2 or 3), $(HOOC-CH_2)_2CH$, $(HO-CH_2)_2CH$, HOOC—$CH_2$—CH(COOH), HO—$CH_2CH_2$—CH(COOH), HOOC—CH ($C_{1-4}$-alkyl), $C_{1-4}$-alkyl-OOC—$CH_2$ or benzyl-OOC—$CH_2$.

5. The compound of the formula I defined in claim 1, wherein the moiety —$NR^4$—$CR^5R^6$—CO— represents one of the following groups:

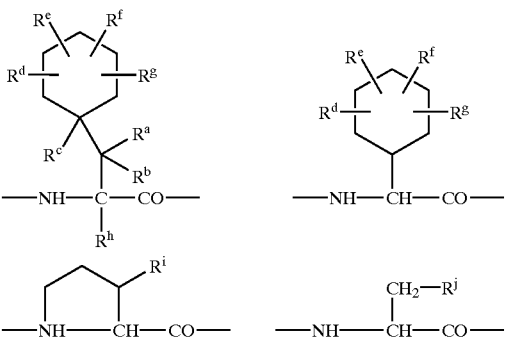

wherein $R^a$ and $R^b$ are independently from one another hydrogen, cyclohexyl or $C_{1-4}$-alkyl, $R^c$, $R^d$, $R^e$, $R^f$, $R^g$ and $R^h$ are independently from one another hydrogen or $C_{1-4}$-alkyl, and wherein the carbon ring members of the cyclohexyl moiety are unsubstituted or mono- or disubstituted, $R^i$ is phenyl or cyclohexyl, and $R^j$ is cyclopentyl, cycloheptyl, 1-adamantyl, 1-norbornyl, 1-bicyclo[2.2.2]octyl, neopentyl, tert-butyl, diisopropylmethyl or 1-(1,4-cyclohexadienyl).

6. The compound of the formula I defined in claim 5, wherein the amino acid moiety represented by —$NR^4$—$CR^5R^6$—CO— is in the D configuration.

7. The compound of the formula I defined in claim 1, wherein l is 0.

8. The compound of the formula I defined in claim 1, wherein R is hydrogen or methyl.

9. The compound of the formula I defined in claim 1, wherein $R^1$ is COOH, l, m and n are 0, $R^2$, $R^3$ and $R^4$ are hydrogen, $R^5$ is cyclohexylmethyl, and $R^6$ and R are hydrogen.

10. A composition comprising a thrombin inhibitory amount of the compound I defined in claim 1 and a conventional pharmaceutical auxiliary.

11. An article having an artificial surface, which article is selected from the group consisting of a membrane, tube or line for hemodialysis, a membrane, tube or line for an oxygenator in extravascular circulation, a stent and a heart valve, wherein the artificial surface is coated with a thrombin inhibitory amount of the compound of the formula I defined in claim 1.

12. A method of inhibiting thrombin comprising administering to a mammal in need thereof compound defined in claim 1 for a time and under conditions effective to inhibit thrombin.

13. A method of inhibiting fibrin formation comprising administering to a mammal in need thereof the compound defined in claim 1 for a time and under conditions effective to inhibit thrombin.

14. A method of inhibiting thrombin in a mammal afflicted with a thrombin-dependent thromboembolic disorder selected from the group consisting of deep vein thromboses, pulmonary embolism, myocardial infarct, cerebral infarct, unstable angina and dissiminated intravascular coagulation, which method comprises administering to said mammal the compound defined in claim 1 for a time and under conditions effective to inhibit thrombin.

15. A compound of the formula II

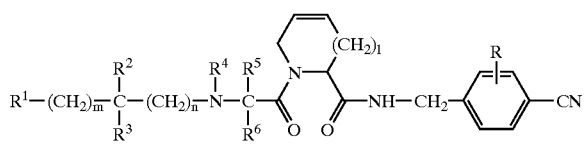

(II)

wherein l is 0 or 1, m is 0, 1 or 2, n is 0, 1 or 2,

R is hydrogen or $C_{1-4}$-alkyl, $R^1$ is HOOC—, $C_{1-6}$-alkyl-OOC, benzyl-OOC or hydroxyl, $R^2$ is hydrogen, $C_{1-4}$-alkyl or $R^1$—$(CH_2)_m$, $R^3$ is hydrogen or $C_{1-4}$-alkyl which is unsubstituted or substituted by hydroxyl or COOH, $R^4$ is hydrogen, $C_{1-4}$-alkyl-, HOOC—$C_{1-4}$-alkylene-, $R^5$ is $C_{1-8}$-alkyl, cycloalkyl-$(CR^8R^9)_r$ (r=0 or 1, $R^8$, $R^9$=hydrogen, cycloalkyl or $C_{1-4}$-alkyl), wherein up to four $CH_2$ groups of the cycloalkyl radical may be replaced, independently from one another, by $CR^{10}R^{11}$ ($R^{10}$=hydrogen or $C_{1-4}$-alkyl, $R^{12}$=$C_{1-4}$-alkyl) and/or the CH group in the cycloalkyl radical which is bonded to $CR^8R^9$ may be replaced by $CR^{12}$ ($R^{12}$=$C_{1-4}$-alkyl), and/or one or two C—C single bond(s) of the cycloalkyl ring may be replaced by a C=C double bond, $R^6$ is hydrogen, $C_{1-4}$-alkyl, or $R^4$ and $R^5$ are together $CH_2$—$CH_2$—$CH(R^7)$, ($R^7$=hydrogen, phenyl or cyclohexyl), or $R^2$ and $R^5$ are together $CH_2$—$CH_2$ or $CH_2$—$CH_2$—$CH_2$—, in which one hydrogen atom may be replaced by $C_{1-4}$-alkyl, phenyl or cycloalkyl.

16. A compound of the formula III

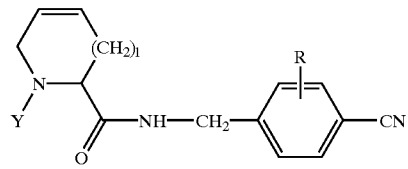

(III)

wherein l is 0 or 1,

R is hydrogen or $C_{1-4}$-alkyl, and

Y is an N protective group, an N-terminally protected or unprotected amino acid or hydrogen.

* * * * *

UNITED STATES PATENT AND TRADEMARK OFFICE
CERTIFICATE OF CORRECTION

PATENT NO.     : 6,440,937 B1
DATED          : August 27, 2002
INVENTOR(S)    : Baucke et al.

It is certified that error appears in the above-identified patent and that said Letters Patent is hereby corrected as shown below:

Column 20,
Line 43, delete "pharmaceutical".
Line 52, after "thereof" insert -- the --.
Line 54, "dissiminated" should be -- disseminated --.

Column 21,
Line 27, "$R^{12}=C_{1-4}$-alkyl" should be -- $R^{11}=C_{1-4}$-alkyl --.

Signed and Sealed this

Twenty-fourth Day of December, 2002

JAMES E. ROGAN
*Director of the United States Patent and Trademark Office*